US011614388B2

(12) United States Patent
Inuzuka et al.

(10) Patent No.: US 11,614,388 B2
(45) Date of Patent: Mar. 28, 2023

(54) METHOD FOR RECOVERING EXTRACELLULAR VESICLES

(71) Applicant: H.U. GROUP RESEARCH INSTITUTE G.K., Hachioji (JP)

(72) Inventors: Tatsutoshi Inuzuka, Tokyo (JP); Ayako Kurimoto, Tokyo (JP)

(73) Assignee: H.U. GROUP RESEARCH INSTITUTE G.K., Hachioji (JP)

( * ) Notice: Subject to any disclaimer, the term of this patent is extended or adjusted under 35 U.S.C. 154(b) by 547 days.

(21) Appl. No.: 16/340,217

(22) PCT Filed: Oct. 12, 2017

(86) PCT No.: PCT/JP2017/037021
§ 371 (c)(1),
(2) Date: Apr. 8, 2019

(87) PCT Pub. No.: WO2018/070479
PCT Pub. Date: Apr. 19, 2018

(65) Prior Publication Data
US 2020/0041391 A1 Feb. 6, 2020

(30) Foreign Application Priority Data
Oct. 13, 2016 (JP) .............................. JP2016-202043

(51) Int. Cl.
*G01N 1/34* (2006.01)
*G01N 33/68* (2006.01)
*C12Q 1/6806* (2018.01)

(52) U.S. Cl.
CPC ............. *G01N 1/34* (2013.01); *C12Q 1/6806* (2013.01); *G01N 33/68* (2013.01)

(58) Field of Classification Search
CPC .................................................. C12Q 1/6806
See application file for complete search history.

(56) References Cited

U.S. PATENT DOCUMENTS

| | | | | |
|---|---|---|---|---|
| 9,487,837 B2 * | 11/2016 | Newman | .......... | G01N 33/56983 |
| 10,794,899 B2 * | 10/2020 | Nishibu | .................... | C12N 7/02 |
| 2009/0220944 A1 | 9/2009 | Fais et al. | | |
| 2010/0086956 A1 * | 4/2010 | Newman | .......... | G01N 33/56988 204/464 |
| 2015/0125864 A1 * | 5/2015 | Kang | ..................... | G01N 1/405 435/6.12 |
| 2015/0353920 A1 | 12/2015 | Enderle et al. | | |
| 2017/0146543 A1 | 5/2017 | Lozupone et al. | | |

FOREIGN PATENT DOCUMENTS

| | | | |
|---|---|---|---|
| CN | 105026911 A | 11/2015 | |
| JP | 2011-510309 A | 3/2011 | |
| WO | WO 2015/185730 A2 | 12/2015 | |
| WO | WO-2016088689 A1 * | 6/2016 | ............... B62D 5/04 |

OTHER PUBLICATIONS

Ian D R Fry and Bryan J Starkey, The determination of oxalate in urine and plasma by high performance liquid chromatography, 1991, An Clin Biochem, 28:581-587 (Year: 1991).*
Toko Shimizu, Elevated Levels of Anti-CD9 antibodies in the cerebrospinal fluid of patients with subacute sclerosing panencephalitis, 2002, J Infect Dis, vol. 185, p. 1346-1350 (Year: 2002).*
Alexander Stoeck, a role for exosomes in the constitutive and stimulus-induced ectodomain cleavage of L1 and CD44, 2006, vol. 393, p. 609-618 (Year: 2006).*
Kurimoto et al., Enhanced recovery of CD9-positive extracellular vesicles from human specimens by chelating reagent, 2020, BioRxiv, posted Jun. 8, 2020, pp. 1-15 (Year: 2020).*
Extended European Search Report dated May 4, 2020 in Patent Application No. 17860942.6, 9 pages.
Jongmin Kim, et al., "Isolation of High-Purity Extracellular Vesicles by Extracting Proteins Using Aqueous Two-Phase System" Plos One, vol. 10, No. 6, XP055504906, Jun. 19, 2015, pp. 1-16.
Hyunwoo Shin, et al., "High-Yield Isolation of Extracellular Vesicles Using Aqueous Two-Phase System" Scientific Reports, vol. 5, No. 1, XP055479252, Aug. 14, 2015, 11 pages.
Rong Xu, et al., "Extracellular Vesicle Isolation and Characterization: Toward Clinical Application" The Journal of Clinical Investigation, vol. 126, No. 4, XP055500209, Apr. 1, 2016, pp. 1152-1162.
Rafal Szatanek, et al., "Isolation of Extracellular Vesicles: Determining the Correct Approach (Review)" International Journal of Molecular Medicine, vol. 36, No. 1, XP055409099, Jul. 1, 2015, pp. 11-17.
International Search Report dated Jan. 16, 2018 in PCT/JP2017/037021 filed on Oct. 12, 2017.
Combined Chinese Office Action and Search Report dated Nov. 28, 2019, in Patent Application No. 201780060943.5, 13 pages (with English translation).
Prachayasittikul, V. et al., "EDTA-induced Membrane Fluidization and Destabilization: Biophysical Studies on Artificial Lipid Membranes", Institute of Biochemistry and Cell Biology, vol. 39, No. 11, 2007, pp. 901-913.
Combined Chinese Office Action and Search Report dated Jul. 1, 2020 in Patent Application No. 201780060943.5 (with English language translation), 15 pages.

* cited by examiner

*Primary Examiner* — Narayan K Bhat
(74) *Attorney, Agent, or Firm* — Oblon, McClelland, Maier & Neustadt, L.L.P.

(57) ABSTRACT

The present invention provides recovering an extracellular vesicle(s) having high purity from an extracellular vesicle-containing sample. Specifically, the present invention provides a method of recovering an extracellular vesicle(s), comprising:

(1) treating an extracellular vesicle-containing sample with a chelating agent; and (2) separating the extracellular vesicle(s) from the extracellular vesicle-containing sample treated with the chelating agent.

22 Claims, 9 Drawing Sheets

• control

• EDTA/EGTA

METHOD FOR RECOVERING EXTRACELLULAR VESICLES

TECHNICAL FIELD

The present invention relates to a method of recovering extracellular vesicles, and the like.

BACKGROUND ART

An extracellular vesicle is a microscopic vesicle secreted from various types of cells and having a membrane structure, and exists in body fluids such as blood. The extracellular vesicles secreted extracellularly include exosomes, ectosomes, and apoptotic blebs. Since the extracellular vesicle contains various substances that play a function such as intercellular signaling, it has been analyzed for the purposes of diagnosis, drug discovery and the like. Thus, it is required to develop a method of treating the extracellular vesicles useful for such analyses. For example, Patent Literature 1 describes that a chelating agent (e.g., EDTA) is used for stabilizing the extracellular vesicles.

PRIOR ART REFERENCES

Patent Literatures

Patent Literature 1: US Patent Application Publication No. 2015/0125864

SUMMARY OF INVENTION

Problem to be Solved by the Invention

If extracellular vesicles of high purity can be recovered from an extracellular vesicle-containing sample, such extracellular vesicles are promising for application to diagnosis, drug discovery and the like. The extracellular vesicle is primarily recovered by an immunoprecipitation method using an antibody against an extracellular vesicle marker or an ultracentrifugation method. However, such a method varies in quality and does not always have high purity for recovered extracellular vesicles.

Therefore, it is an object of the present invention to develop a method of recovering the extracellular vesicles with high purity.

In addition, it is another object of the present invention to develop a method of being able to recover the extracellular vesicles that are more homogeneous in quality.

Means for Solving Problem

As a result of an extensive study, the present inventors have found that extracellular vesicles can be recovered with high purity by treating an extracellular vesicle-containing sample with a chelating agent followed by recovering them, and completed the present invention.

That is, the present inventions are as follows.

[1] A method of recovering an extracellular vesicle(s), comprising:
(1) treating an extracellular vesicle-containing sample with a chelating agent; and
(2) separating the extracellular vesicle(s) from the extracellular vesicle-containing sample treated with the chelating agent.

[2] The method described in [1], wherein the chelating agent is selected from the group consisting of ethylenediaminetetraacetic acid (EDTA), glycoletherdiaminetetraacetic acid (EGTA), hydroxyethyl ethylenediaminetriacetic acid (HEDTA), hydroxyethyliminodiacetic acid (HIDA), nitrilotriacetic acid (NTA), oxalic acid, ethylenediaminetetra(methylenephosphonic acid) (EDTMP), and salts thereof, and mixtures thereof.

[3] The method described in [1] or [2], wherein the extracellular vesicle-containing sample is treated with 1 to 200 mM of the chelating agent.

[4] The method described in [3], wherein the extracellular vesicle-containing sample is treated with 20 to 200 mM of the chelating agent.

[5] The method described in any one of [1] to [4], wherein the extracellular vesicle(s) is an exosome(s).

[6] The method described in any one of [1] to [5], wherein the separation is performed by a precipitation method using an extracellular vesicle membrane-binding substance or an ultracentrifugation method of the extracellular vesicle-containing sample.

[7] The method described in [6], wherein the extracellular vesicle membrane-binding substance is an antibody against CD9.

[8] The method described in any one of [1] to [7], wherein the extracellular vesicle-containing sample is a body fluid or a culture supernatant.

[9] The method described in any one of [1] to [7], wherein the extracellular vesicle-containing sample is a blood sample, urine, or a breast fluid.

[10] A method of analyzing an extracellular vesicle(s), comprising:
(1) treating an extracellular vesicle-containing sample with a chelating agent;
(2) separating the extracellular vesicle(s) from the extracellular vesicle-containing sample treated with the chelating agent; and
(3) analyzing the separated extracellular vesicle(s).

[11] The method described in [10], wherein a protein in the separated extracellular vesicle(s) is analyzed.

[12] A kit comprising a chelating agent and an extracellular vesicle membrane-binding substance.

[13] A method of inhibiting binding of an extracellular vesicle(s) to an extracellular vesicle-adsorbing protein, comprising treating the extracellular vesicle(s) having the extracellular vesicle-adsorbing protein bound thereto with a chelating agent to dissociate the extracellular vesicle-adsorbing protein from the extracellular vesicle(s),
wherein the extracellular vesicle-adsorbing protein is one or more proteins selected from the group consisting of albumin, synaptotagmin-like protein 4, vitronectin, cell division control protein 2 homolog, trypsin-2, immunoglobulin µ heavy chain disease protein, α-1B-glycoprotein, immunoglobulin κ chain V-III region WOL, hemopexin, antithrombin-III, prothrombin, gelsolin, complement C1 subcomponent, complement factor B, complement component C9, ficolin-2, serum paraoxonase/arylesterase 1, immunoglobulin κ chain V-I region Daudi, and immunoglobulin heavy chain V-III region TUR.

[14] A free natural extracellular vesicle(s), wherein one or more extracellular vesicle-adsorbing proteins selected from the group consisting of albumin, synaptotagmin-like protein 4, vitronectin, cell division control protein 2 homolog, trypsin-2, immunoglobulin µ heavy chain disease protein, α-1B-glycoprotein, immunoglobulin κ chain V-III region WOL, hemopexin, antithrombin-III, prothrombin, gelsolin, complement C1 subcomponent, complement factor B, complement component C9, ficolin-2, serum paraoxonase/ arylesterase 1, immunoglobulin κ chain V-I region Daudi, and immunoglobulin heavy chain V-III region TUR are dissociated.

[15] The extracellular vesicle(s) described in [14], wherein all extracellular vesicle-adsorbing proteins selected from said group are dissociated.

[16] The extracellular vesicle(s) described in [14] or [15], wherein a dissociation degree of the extracellular vesicle-adsorbing proteins from said extracellular vesicle(s) is 50% or more.

[17] The extracellular vesicle(s) described in any one of [14] to [16], wherein said extracellular vesicle(s) is isolated or purified.

[18] The extracellular vesicle(s) described in any one of [14] to [17], wherein said extracellular vesicle(s) is an exosome.

[19] The extracellular vesicle(s) described in any one of [14] to [16], wherein said extracellular vesicle(s) is obtained by a method comprising:
(1) treating an extracellular vesicle-containing sample with a chelating agent; and
(2) separating the extracellular vesicle(s) from the extracellular vesicle-containing sample treated with the chelating agent.

[20] A solution:
(A) comprising a free natural extracellular vesicle(s), wherein one or more extracellular vesicle-adsorbing proteins selected from the group consisting of albumin, synaptotagmin-like protein 4, vitronectin, cell division control protein 2 homolog, trypsin-2, immunoglobulin μ heavy chain disease protein, α-1B-glycoprotein, immunoglobulin κ chain V-III region WOL, hemopexin, antithrombin-III, prothrombin, gelsolin, complement C1 subcomponent, complement factor B, complement component C9, ficolin-2, serum paraoxonase/arylesterase 1, immunoglobulin κ chain V-I region Daudi, and immunoglobulin heavy chain V-III region TUR are dissociated; and
(B) not comprising said one or more extracellular vesicle-adsorbing proteins.

Effect of the Invention

Adsorption of concomitant substances to the extracellular vesicles to be recovered can be reduced by treating the extracellular vesicle-containing sample with the chelating agent. Therefore, according to the present invention, the extracellular vesicles can be recovered with high purity. Types and amounts of extracellular vesicle-adsorbing proteins included in the extracellular vesicle-containing sample are thought to vary depending on a type of the extracellular vesicle-containing sample, a type of an organism which the extracellular vesicle-containing sample is derived from, and a state of the organism which the extracellular vesicle-containing sample is derived from. According to the present invention, binding of various adsorbing proteins to the extracellular vesicles can be inhibited. Therefore, according to the present invention, it is thought that recovery of the extracellular vesicles that are more homogeneous in quality becomes possible.

EMBODIMENTS FOR CARRYING OUT THE INVENTION

Figure 1:
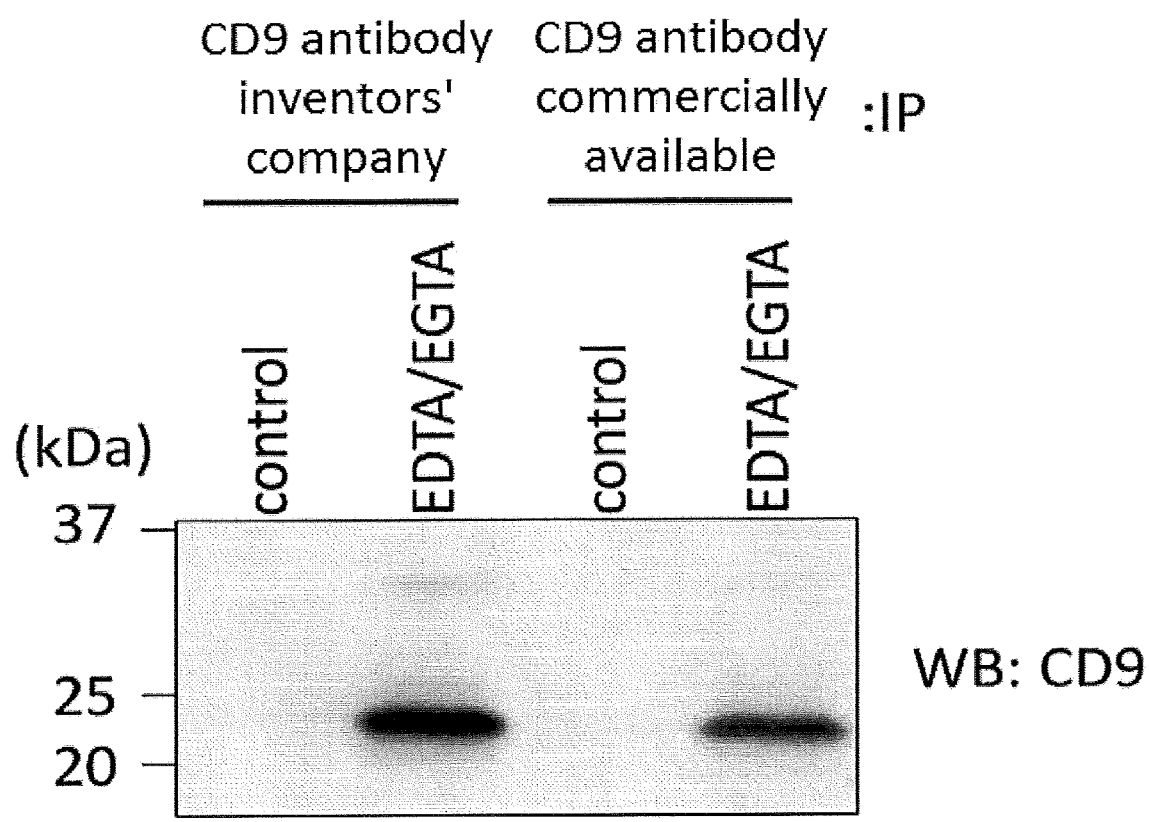
FIG. 1 shows a western blotting (WB) with a biotinylated anti-CD9 antibody of samples obtained from an immunoprecipitation (IP) method of serum specimens diluted with PBS ("control") or EDTA/EGTA/PBS ("EDTA/EGTA") in Example 1.

The present invention provides a method of recovering extracellular vesicle(s).

An extracellular vesicle(s) is a microscopic vesicle(s) secreted from various types of cells and having a membrane structure. Examples of the extracellular vesicle(s) include exosome(s), ectosome(s) and apoptotic bleb(s). Preferably, the extracellular vesicle(s) is the exosome(s). The extracellular vesicle(s) can be also defined by its size. The size of the extracellular vesicle(s) is, for example, 30 to 1000 nm, preferably 50 to 300 nm, and more preferably 80 to 200 nm. The size of the extracellular vesicle(s) can be measured by, for example, a method based on Brownian movement of the extracellular vesicle(s), a light scattering method, and an electric resistance method, and the like. Preferably, the size of the extracellular vesicle(s) is measured by NanoSight (manufactured by Malvern Instruments).

The recovering method of the present invention comprises the following steps:

(1) treating an extracellular vesicle-containing sample with a chelating agent; and
(2) separating extracellular vesicle(s) from the extracellular vesicle-containing sample treated with the chelating agent.

The extracellular vesicle-containing sample is any sample that contains the extracellular vesicles. Preferably, the extracellular vesicle-containing sample is a biological liquid sample. The extracellular vesicle-containing sample may be subjected to another treatment before being used for the method of the present invention. Examples of such a treatment include centrifugation, extraction, filtration, precipitation, heating, freezing, refrigeration, and stirring.

In one embodiment, the extracellular vesicle-containing sample is a culture supernatant. The culture supernatant may be a cell culture supernatant or a tissue culture supernatant. Organisms which a cell or tissue to be cultured is derived from include, for example, animals such as mammalian animals (e.g., primates such as humans and monkeys; rodents such as mice, rats and rabbits; farm animals such as cattle, pigs and goats; and working animals such as horses and sheep) and birds (e.g., chickens), insects, microorganisms (e.g., bacteria), plants and fish. Preferably, the organisms are mammalian animals such as humans.

In another embodiment, the extracellular vesicle-containing sample is a body fluid. The body fluid is derived from the organism as described above. Examples of the body fluid include blood samples (e.g., whole blood, serum and plasma), lymph fluid, tissue fluid, cerebrospinal fluid, ascites, saliva, sweat, seminal fluid, urine, tear fluid, mucosal fluid, breast fluid, thoracic fluid, bronchoalveolar lavage fluid and amnion fluid. Preferably, the body fluid is the blood. In general, recovery of the extracellular vesicle(s) is more difficult in the body fluid (e.g., blood, urine, breast fluid) in which proteins (e.g., albumin, casein, lactalbumin, lactoferrin) in larger amount than in the culture supernatant are mixed compared with that in the culture supernatant. However, according to the method of the present invention, the extracellular vesicles can be recovered with high purity even from such a body fluid.

In still another embodiment, the extracellular vesicle-containing sample is a sample further comprising one or more extracellular vesicle-adsorbing proteins as concomitant substances in addition to the extracellular vesicles. The extracellular vesicle-adsorbing protein means a protein having an ability to directly adsorb to an extracellular vesicle or a protein having an ability to adsorb to an extracellular vesicle indirectly via another factor (e.g., a protein). Examples of the extracellular vesicle-adsorbing protein include albumin, synaptotagmin-like protein 4, vitronectin, cell division control protein 2 homolog, trypsin-2, immunoglobulin μ heavy chain disease protein, α-1B-glycoprotein, immunoglobulin κ chain V-III region WOL, hemopexin, antithrombin-III, prothrombin, gelsolin, complement C1 subcomponent, complement factor B, complement component C9, ficolin-2, serum paraoxonase/arylesterase 1, immunoglobulin κ chain V-I region Daudi, and immunoglobulin heavy chain V-III region TUR. Types and amounts of the extracellular vesicle-adsorbing proteins included in the extracellular vesicle-containing sample are thought to vary depending on a type of the extracellular vesicle-containing sample (e.g., body fluid such as blood, and culture supernatant), a type of an organism which the extracellular vesicle-containing sample is derived from, and a state of the organism which the extracellular vesicle-containing sample is derived from (e.g., health condition, abnormal condition such as a particular disease, and the like). According to the present invention, it is possible to inhibit binding of various adsorbing proteins to the extracellular vesicle. Thus, according to the present invention, it is thought that recovery of the extracellular vesicles that are more homogeneous in quality becomes possible.

A chelating agent is a compound or a salt thereof having a coordinate portion in which a coordinate bond to a metal ion can be made. The number of the coordinate portions is preferably 2 or more, and more preferably 3 or more (e.g., 3 or 6). Examples of the coordinate atom as the coordinate portion include an oxygen atom, a phosphorus atom, a nitrogen atom, a sulfur atom, and a chlorine atom. The coordinate atom is preferably the oxygen atom or phosphorus atom, and more preferably the oxygen atom. Examples of the coordinate group as the coordinate portion include groups having the above coordinate atom. The coordinate group is preferably a carboxylate group or a phosphate group, and more preferably the carboxylate group.

Examples of the chelating agent include oxalic acid, hydroxyethyliminodiacetic acid (HIDA), nitrilotriacetic acid (NTA), hydroxyethyl ethylenediaminetriacetic acid (HEDTA), ethylenediaminetetraacetic acid (EDTA), ethylenediaminetetra(methylenephosphonic acid) (EDTMP), glycoletherdiaminetetraacetic acid (EGTA), and salts thereof. Examples of the salts include metal salts (e.g., monovalent metal salts such as sodium salts, potassium salts, and bivalent metal salts such as calcium salts, magnesium salts), inorganic salts (e.g., halide salts such as fluoride, chloride, bromide and iodide, and ammonium salts), organic salts (e.g., ammonium salts substituted with an alkyl group), and acid addition salts (e.g., salts with an inorganic acid such as sulfuric acid, hydrochloric acid, hydrobromic acid, nitric acid, phosphoric acid and the like, and salts with an organic acid such as acetic acid, oxalic acid, lactic acid, citric acid, trifluoromethanesulfonic acid, trifluoroacetic acid and the like). In the present invention, a mixture of 2 or more (e.g., 2, 3, 4, 5) chelating agents may be used for the treatment of the extracellular vesicle-containing sample. In the present invention, the method may comprise adding the chelating agent to the extracellular vesicle-containing sample prior to the treatment of the extracellular vesicle-containing sample.

A concentration of the chelating agent in the treatment of the extracellular vesicle-containing sample is not particularly limited as long as the adsorption of the concomitant substances to the extracellular vesicles can be inhibited and the chelating agent can be dissolved in a solution used for the treatment. Such a concentration varies depending on a type of the chelating agent, but is, for example, 1 mM to 200 mM. Preferably, the concentration of the chelating agent may be 10 mM or more, 15 mM or more, 20 mM or more, 30 mM or more, 40 mM or more, or 50 mM or more. Such a concentration varies depending on a type of the chelating agent, but may be 200 mM or less, 180 mM or less, 160 mM or less, 140 mM or less, 120 mM or less, or 100 mM or less.

A temperature in the treatment of the extracellular vesicle-containing sample is, for example, 4 to 37° C., and may preferably be 15 to 30° C. A time period for the treatment is not particularly limited as long as it is enough to inhibit the adsorption of the concomitant substances to the extracellular vesicles, and may be, for example, 1 minute or more, 5 minutes or more, 10 minutes or more or 20 minutes or more. Such a time period may be 4 hours or less, 2 hours or less, or one hour or less. After mixing the extracellular vesicle-containing sample with the chelating agent, the mixed solution may be left to stand in the treatment of the extracellular vesicle-containing sample.

The extracellular vesicle(s) can be separated from the extracellular vesicle-containing sample treated with the chelating agent by, for example, a precipitation method using an extracellular vesicle membrane-binding substance, or an ultracentrifugation method. The extracellular vesicle(s) can be recovered by precipitating the extracellular vesicle(s) by the precipitation method or the ultracentrifugation method and then collecting a precipitate or discarding a supernatant. The separation is preferably isolation or purification. Therefore, the recovering method of the present invention can be utilized as an isolation method or a purification method.

The extracellular vesicle membrane-binding substance used in the precipitation method is a substance having an affinity to an extracellular vesicle marker. Examples of the extracellular vesicle marker include CD9, carcinoembryonic antigen (CEA), CD81, CD63, heat shock protein (HSP) 70, HSP 90, major histocompatibility complex (MHC) I, tumor susceptibility gene (TSG) 101, lysosome-associated membrane protein (LAMP) 1, intercellular adhesion molecule (ICAM)-1, integrin, ceramide, cholesterol, phosphatidylserine, ALIX, Annexins, Caveolin-I, Flotillin-I, Rab proteins, EpCAM, and the like. Examples of the extracellular vesicle membrane-binding substance include antibodies (e.g., monoclonal antibody, polyclonal antibody), aptamers, phosphatidylserine-binding proteins, and ceramide-binding proteins. The extracellular vesicle membrane-binding substance is preferably an antibody, and more preferably a monoclonal antibody. When the antibody is used as the extracellular vesicle membrane-binding substance, the precipitation method is an immunoprecipitation method. The extracellular vesicle membrane-binding substance may be bound to a solid phase (e.g., magnetic beads) for allowing aggregation easy.

Ultracentrifugation can be carried out using an ultracentrifuge. A gravity force applied in the ultracentrifugation is, for example, 10,000×g to 200,000×g, and preferably may be 70,000×g to 150,000×g. A time period for the ultracentrifugation is, for example, 0.5 to 24 hours, and preferably 1 to 5 hours. A temperature for the ultracentrifugation is, for example, 4 to 30° C. The ultracentrifugation may be carried out once or multiple times (e.g., twice, three times).

The present invention also provides a method of analyzing an extracellular vesicle(s).

The analyzing method of the present invention comprises the followings:
(1) treating an extracellular vesicle-containing sample with a chelating agent;
(2) separating the extracellular vesicle(s) from the extracellular vesicle-containing sample treated with the chelating agent; and
(3) analyzing the separated extracellular vesicle(s).

(1) and (2) in the analyzing method of the present invention can be carried out in the same manner as in (1) and (2) in the recovering method of the present invention.

In (3), the separated extracellular vesicle(s) is analyzed. Targets to be analyzed include, for example, components included in the extracellular vesicle(s) (e.g., components included inside the extracellular vesicle(s), membrane components of the extracellular vesicle(s), components present on a membrane surface of the extracellular vesicle(s)), and the extracellular vesicle(s) itself (particle).

When the component included in the extracellular vesicle(s) is analyzed, the analysis is detection or quantitative determination of the component. Such an analysis is an analysis of one component or multiple components. Examples of the components to be analyzed include proteins, nucleic acids (e.g., RNA, DNA), sugars, lipids, amino acids, vitamins, polyamine, and peptides. The extracellular vesicle(s) separated from the extracellular vesicle-containing sample treated with chelating agent excludes protein concomitant substances in particular. Therefore, according to the analyzing method of the present invention, effects of the protein concomitant substances are excluded, thereby being capable of analyzing the proteins with high accuracy in the extracellular vesicle(s).

The analysis of the component can be carried out by any method known in the art. When the component to be analyzed is a protein, examples of the analyzing method include immunoassay and mass spectrometry. Examples of the immunoassay include a direct competition method, an indirect competition method, and a sandwich method. Such an immunoassay also includes chemiluminescence immunoassay (CLIA) [e.g., chemiluminescence enzyme immunoassay (CLEIA)], turbidimetric immunoassay (TIA), enzyme immunoassay (EIA) [e.g., direct competitive ELISA, indirect competitive ELISA, and sandwich ELISA], radioimmunoassay (RIA), latex aggregation reaction method, fluorescence immunoassay (FIA), and immunochromatographic method, western blotting, immunostaining, and fluorescence activated cell sorting (FACS). When multiple components are analyzed, a proteome analysis may be carried out.

When a component to be analyzed is a nucleic acid, examples of the analyzing method include a hybridization method using a probe, gene amplification method using primers (e.g., 2, 3 or 4 primers), and mass spectrometry.

When a component to be analyzed is a component other than proteins and nucleic acids, examples of the analyzing method include immunoassay and mass spectrometry. When multiple components are analyzed, a metabolome analysis may be carried out.

The analysis of the extracellular vesicle(s) itself (particle) can be carried out by, for example, instruments such as a particle analytical instrument, an electron microscope and a flow cytometer. In this case, particle counts, particle sizes and shapes of the extracellular vesicles and their distribution can be analyzed.

The extracellular vesicle(s) has been reported to be able to be involved in various diseases such as cancers (International Publication WO2014/003053; International Publication WO2014/152622; Taylor et al., Gynecologic Oncol., 100 (2008) pp 13-21). Therefore, the recovering method and the analyzing method of the present invention are useful for diagnosis and drug discovery based on the extracellular vesicles.

The present invention also provides a method of inhibiting binding of an extracellular vesicle(s) to an extracellular vesicle-adsorbing protein.

The inhibiting method of the present invention comprises treating an extracellular vesicle(s) having an extracellular vesicle-adsorbing protein bound thereto with a chelating agent to dissociate the extracellular vesicle-adsorbing protein from the extracellular vesicle. Examples of the extracellular vesicle-adsorbing protein include albumin, synaptotagmin-like protein 4, vitronectin, cell division control protein 2 homolog, trypsin-2, immunoglobulin μ heavy chain disease protein, α-1B-glycoprotein, immunoglobulin κ chain V-III region WOL, hemopexin, antithrombin-III, prothrombin, gelsolin, complement C1 subcomponent, complement factor B, complement component C9, ficolin-2, serum paraoxonase/arylesterase 1, immunoglobulin κ chain V-I region Daudi, and immunoglobulin heavy chain V-III region TUR. As described above, it is thought that it becomes possible to recover the extracellular vesicles that are more homogeneous in quality. Thus, the inhibiting method of the present invention is useful for performing the recovering method and the analyzing method of the present invention and for screening of pharmaceuticals using the extracellular vesicles, for example.

The present invention also provides a kit comprising the chelating agent and the extracellular vesicle membrane-binding substance as described above. The kit of the present invention is useful, for example, for simply performing the recovering method, the analyzing method and the inhibiting method of the present invention as well as for simple preparation of the extracellular vesicle(s) and a solution of the present invention as described later.

The present invention also provides a free natural extracellular vesicle(s). One or more extracellular vesicle-adsorbing proteins described above have adsorbed to the extracellular vesicle of the present invention. One or more, preferably 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, or all of these extracellular vesicle-adsorbing proteins may be dissociated from the extracellular vesicle of the present invention.

The extracellular vesicle(s) of the present invention can be defined by a dissociation degree (%) of the extracellular vesicle-adsorbing proteins from the extracellular vesicle. The dissociation degree (%) of the extracellular vesicle-adsorbing proteins from the extracellular vesicle(s) can be calculated by a formula of [(total amount of extracellular vesicle-adsorbing proteins dissociated from the extracellular vesicles by treating extracellular vesicles in extracellular vesicle-containing sample with chelating agent)/(total amount of extracellular vesicle-adsorbing proteins naturally adsorbed to extracellular vesicles in extracellular vesicle-containing sample)]×100%. Here, a percentage value of [(total amount of extracellular vesicle-adsorbing proteins dissociated from the extracellular vesicles by treating the extracellular vesicles with chelating agent in extracellular vesicle-containing sample)/(total amount of extracellular vesicle-adsorbing protein naturally adsorbed to extracellular vesicles in extracellular vesicle-containing sample)] can be evaluated indirectly by, for example, an immunological method (e.g., western blotting). This is because it is thought that masking of the extracellular vesicles with the extracellular vesicle-adsorbing proteins is released in proportion to an amount of the extracellular vesicle-adsorbing proteins dissociated from the extracellular vesicles to increase an amount of an antibody against an extracellular vesicle marker that is bound to the extracellular vesicles, eventually increase a staining intensity of the extracellular vesicle marker immunostained with the antibody against the extracellular vesicle marker.

Specifically, procedures are as follows. First, a concentration of a chelating agent is increased until an immunostaining intensity of an extracellular vesicle marker after treating extracellular vesicles with the chelating agent reaches a plateau, and the immunostaining intensity that has reached the plateau (a) is measured. Thus, (a) corresponds to a value when a dissociation degree is 100%. Next, an immunostaining intensity of the extracellular vesicle marker after treating with the chelating agent at a target concentration (b) is measured. The above percentage value can be obtained indirectly by calculating (b)/(a).

Figure 2A:
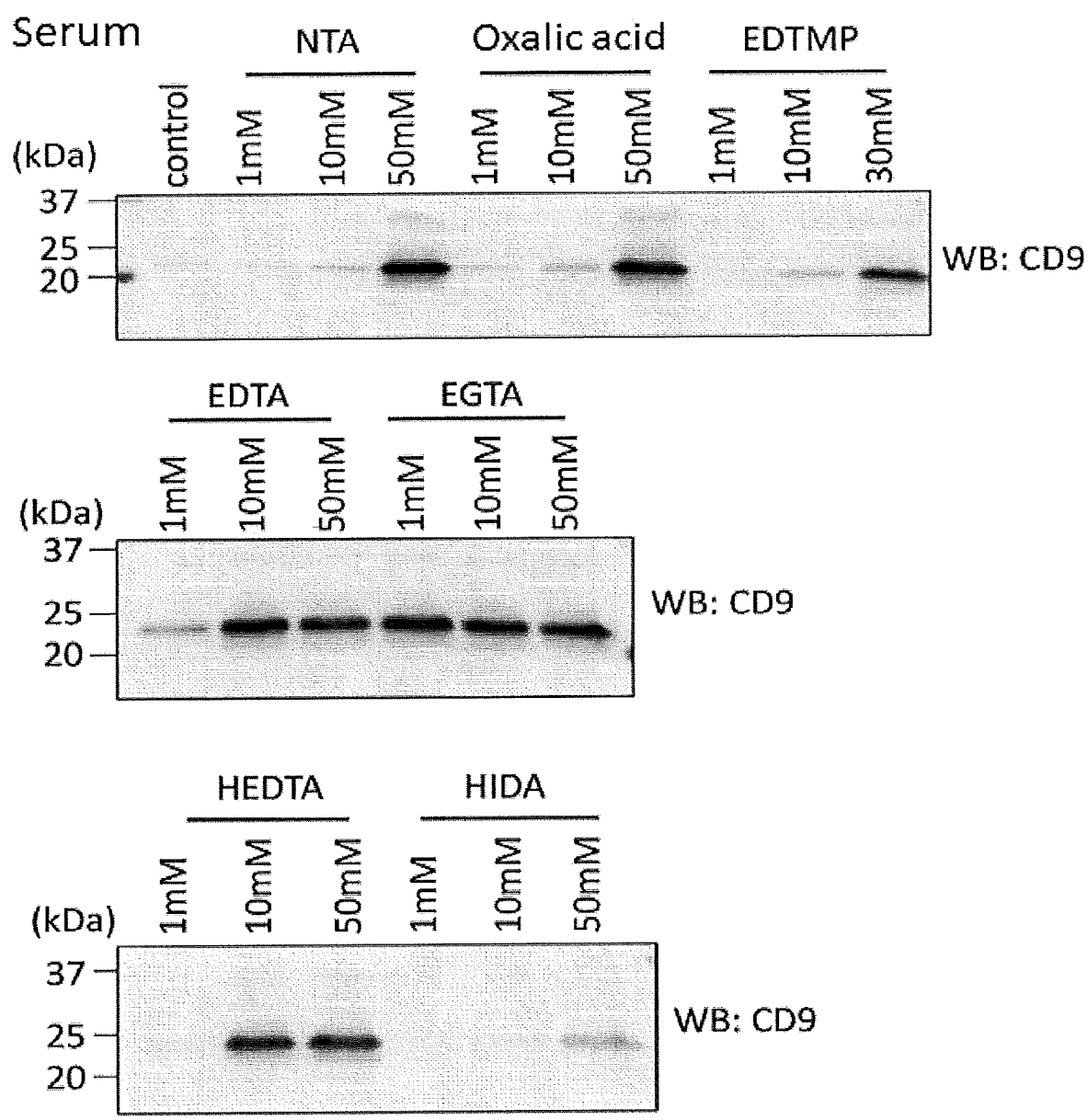
FIG. 2A shows a western blotting with the biotinylated anti-CD9 antibody of samples obtained from the immunoprecipitation method of serum specimens diluted with each chelating agent at each concentration in Example 2.

The above dissociation degree is more specifically explained with reference to a result of immunostaining of EDTA treatment in FIG. 2A. The immunostaining intensity is almost consistent after 10 mM EDTA treatment and 50 mM EDTA treatment, and thus it is understood that the immunostaining intensity based on the extracellular vesicle marker (CD9) has reaches the plateau. Thus, it can be estimated that almost all of the extracellular vesicle-adsorbing proteins (total amount of extracellular vesicle-adsorbing proteins naturally adsorbed to the extracellular vesicles in the extracellular vesicle-containing sample) are dissociated from the extracellular vesicles by 10 mM EDTA treatment. Then, the immunostaining intensity after 1 mM EDTA treatment is about 30% of the immunostaining intensity after 10 mM or 50 mM EDTA treatment. Thus, the dissociation degree of the extracellular vesicle-adsorbing proteins from the extracellular vesicles after 1 mM EDTA treatment can be evaluated to be about 30%.

Concerning the extracellular vesicle(s) of the present invention, the dissociation degree (%) of the extracellular vesicle-adsorbing proteins from the extracellular vesicles varies depending on a type and a concentration of a chelating agent used for the dissociation, but is, for example, 30% or more, preferably 50% or more, more preferably 80% or more, still more preferably 90% or more, most preferably 91% or more, 92% or more, 93% or more, 94% or more, 95% or more, 96% or more, 97% or more, 98% or more, or 99% or more.

The term "free" means that an extracellular vesicle(s) is not immobilized to a solid phase (e.g., support, container, particle). Therefore, an extracellular vesicle(s) directly or indirectly (e.g., through an affinity substance such as an antibody) immobilized to the solid phase is not a free extracellular vesicle(s).

The term "natural" means that an extracellular vesicle(s) has not been modified with an artificial substance or a foreign substance (e.g., a culture supernatant which the extracellular vesicle(s) is derived from, a culture supernatant that is each heterogeneous to body fluid or an organism, an antibody and a fragment thereof derived from the body fluid or the organism; and a labeling substance such as a dye or a fluorescent substance). Therefore, an extracellular vesicle(s) labeled with an artificial substance (e.g., an extracellular vesicle(s) incorporating an artificial substance, an extracellular vesicle(s), a membrane surface of which has been modified with an artificial substance) is not a natural extracellular vesicle(s). On the other hand, an extracellular vesicle(s) from which extracellular vesicle-adsorbing proteins have been dissociated is meant to be taken as a natural extracellular vesicle(s) because it is not labeled with an artificial substance or a foreign substance.

In one embodiment, the extracellular vesicle(s) of the present invention is derived from a culture supernatant. The culture supernatant may be a cell culture supernatant or a tissue culture supernatant. Examples and preferable examples of organisms which cells or tissues to be cultured are derived from are as described above.

In another embodiment, the extracellular vesicle(s) of the present invention is derived from a body fluid. The body fluid is derived from the organisms as described above. Examples and preferable examples of the body fluid are as described above.

Examples and preferable examples of the extracellular vesicle(s) of the present invention are as described above. The extracellular vesicle(s) of the present invention may have the size as described above. The extracellular vesicle(s) of the present invention may have the extracellular vesicle marker as described above.

The extracellular vesicle(s) of the present invention may be isolated or purified one. The isolation or purification of the extracellular vesicle(s) can be carried out by separating the extracellular vesicle(s) from an extracellular vesicle-containing sample treated with a chelating agent by ultracentrifugation. In addition, the extracellular vesicle(s) can be isolated or purified by separating the extracellular vesicle-containing sample treated with the chelating agent by a precipitation method using an extracellular vesicle membrane-binding substance, by ultracentrifugation, and then dissociating the extracellular vesicle(s) (which has been bound to the extracellular vesicle membrane-binding substance in the precipitation method) from the extracellular vesicle-membrane binding substance.

The extracellular vesicle(s) of the present invention can be prepared, for example, by the recovering method of the present invention described above. Since the extracellular vesicle(s) of the present invention has high purity and is homogeneous in quality, it is useful, for example, for screening of pharmaceuticals using the extracellular vesicle(s).

The present invention also provides a solution: (A) comprising a free natural extracellular vesicle(s) from which one or more extracellular vesicle-adsorbing proteins selected from the group consisting of albumin, synaptotagmin-like protein 4, vitronectin, cell division control protein 2 homolog, trypsin-2, immunoglobulin μ heavy chain disease protein, α-1B-glycoprotein, immunoglobulin κ chain V-III region WOL, hemopexin, antithrombin-III, prothrombin, gelsolin, complement C1 subcomponent, complement factor B, complement component C9, ficolin-2, serum paraoxonase/arylesterase 1, immunoglobulin κ chain V-I region Daudi, and immunoglobulin heavy chain V-III region TUR have been dissociated; and (B) not comprising the above one or more extracellular vesicle-adsorbing proteins.

The solution is preferably an aqueous solution. Examples of the aqueous solution include water (e.g., distilled water, sterilized water, sterilized distilled water, pure water), and buffer. Examples of the buffer include phosphate buffer (e.g., PBS), Tris-based buffers such as Tris-HCl buffer and TE (Tris-EDTA) buffer, and carbonate buffer. A pH value of the buffer is adequately around neutral pH values. Such a pH value is, for example, 5.0 to 9.0, preferably 5.5 to 8.5, more preferably 6.0 to 8.0 and still more preferably 6.5 to 7.5. The aqueous solution may comprise an organic solvent (e.g., alcohol) or another component in a small amount. In a certain embodiment, the aqueous solution is preferably an aqueous solution other than the phosphate buffer, and more preferably buffer other than the phosphate buffer. The solution may be provided in a liquid form or a frozen form, but preferably provided in the liquid form.

A volume of the solution may be, for example, 10 μL to 10 mL. Preferably, the volume may be 20 μL or more, 40 μL or more, 50 μL or more, or 100 μL or more. The volume may also be 5 mL or less, 1 mL or less, or 200 μL or less.

In (A), details (definitions, examples, and preferable examples and the like) of the free natural extracellular vesicle(s), and types and dissociation numbers of the extracellular vesicle-adsorbing proteins dissociated from the extracellular vesicles are as described above.

The solution of the present invention may comprise the free natural extracellular vesicles at a predetermined concentration. Such a predetermined concentration may be, for example, $1.0 \times 10^2$ to $1.0 \times 10^{10}$ particles/mL. Preferably, the concentration may be $1.0 \times 10^2$ or more, $1.0 \times 10^3$ or more, $1.0 \times 10^4$ or more, $1.0 \times 10^5$ or more, or $1.0 \times 10^6$ or more. The concentration may also be $1.0 \times 10^9$ particles/mL or less, $1.0 \times 10^8$ particles/mL or less, or $1.0 \times 10^7$ particles/mL or less. The concentration of the extracellular vesicles can be measured by, for example, a method based on a speed of Brownian movement of extracellular vesicles, a light scattering method and an electric resistance method, and the like. Preferably, the size of the extracellular vesicle(s) is measured by NanoSight (manufactured by Malvern Instruments).

The number and types of the extracellular vesicle-adsorbing proteins that are not included in the solution in (B) are the same as the number and types of the extracellular vesicle-adsorbing proteins that have been dissociated from the extracellular vesicles in (A). For example, when the extracellular vesicle-adsorbing proteins that have been dissociated from the extracellular vesicles are albumin, synaptotagmin-like protein 4 and vitronectin in (A), one or more extracellular vesicle-adsorbing proteins that are not included in the solution in (B) are albumin, synaptotagmin-like protein 4 and vitronectin. The extracellular vesicle-adsorbing proteins that are not included in the solution in (B) may be preferably 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, or all.

The solution of the present invention may be one not comprising other substances such as a chelating agent, a labeling substance (e.g., dye, fluorescent substance) and an antibody in addition to the extracellular vesicle-adsorbing proteins described above.

The solution of the present invention can appropriately be prepared. For example, the solution of the present invention can be prepared by isolating or purifying the extracellular vesicles of the present invention, followed by adding the extracellular vesicles of the present invention into a desired solution. The solution of the present invention comprises the extracellular vesicles that have high purity and are homogeneous in quality, and thus is useful, for example, for screening of pharmaceuticals using the extracellular vesicles.

EXAMPLES

Hereinafter, the present invention will be described with reference to Examples, but the present invention is not limited to these Examples.

Example 1

In order to confirm the effects of chelating agent, the influences of chelating agent on the precipitation amount of exosome, which is one of extracellular vesicles, was investigated.

300 μL of a serum specimen was diluted with 600 μL of PBS or EDTA and EGTA-containing PBS (final concentration of EDTA and EGTA: each 50 mM) followed by being left to stand at room temperature for 30 minutes, and then centrifuged at 20,000×g at 4° C. for 15 minutes. The resulting supernatant was transferred to a new tube, and magnetic beads (Protein G Dynabeads, manufactured by Life Technologies) immobilized with each 2 μg of a monoclonal antibody (a monoclonal antibody prepared in the inventors' company or a commercially available monoclonal antibody (manufactured by Cosmo Bio)) recognizing CD9, which is an exosome surface marker, were added thereto. The mixtures were rotation-reacted at 4° C. overnight, then the magnetic beads were washed three times with PBS to elute samples from the magnetic beads, and the samples were diluted with SDS-containing sample buffer (manufactured by BIO-RAD) to use as samples for western blotting. In the samples for western blotting, exosomes are disrupted by treating the samples containing the exosomes with SDS, and exosome marker proteins (e.g., CD9) are released in the sample solutions. The sample derived from the serum specimen diluted with PBS was used as a control, the sample from the serum specimen diluted with EDTA/EGTA/PBS was used as EDTA/EGTA, and both the samples were analyzed by western blotting using a biotinylated anti-CD9 antibody prepared in the inventors' company.

As a result, in the antibody prepared in the inventors' company and the commercially available antibody, the amounts of the immunoprecipitated exosomes (CD9) were drastically increased under the condition of adding the chelating agents (EDTA and EGTA) (FIG. 1).

This result demonstrated that the chelating agent has an effect of enhancing an efficiency of exosome recovery by immunoprecipitation.

Example 2

The relationships of the type and concentration of chelating agent with the immunoprecipitation amount of exosome were investigated.

For chelating agents, disodium ethylenediaminetetraacetate (EDTA.2Na), glycoletherdiaminetetraacetic acid (EGTA), hydroxyethyl ethylenediaminetriacetic acid (HEDTA), hydroxyethyliminodiacetic acid (HIDA), nitrilotriacetic acid (NTA), oxalic acid dihydrate, ethylenediaminetetra (methylenephosphonic acid) (EDTMP) (EDTA.2Na, EGTA were from Dojindo Molecular Technologies, Inc., HEDTA, HIDE, NTA, EDTMP were from Tokyo Chemical Industry Co., Ltd., and oxalic acid dihydrate was from Wako Pure Chemical Industries, Ltd.) were used. The influences of each chelating agent on the precipitation amounts of exosomes were investigated.

300 µL of a serum specimen or a plasma specimen was diluted with 600 µL of PBS or each chelating agent-added PBS. The concentrations of each chelating agent to be used were 1, 10, and 50 mM at final concentrations (provided, 1, 10, and 30 mM only for EDTMP). Then, the solutions were left to stand at room temperature for 30 minutes, and then centrifuged at 20,000×g at 4° C. for 15 minutes. The resulting supernatant was transferred to a new tube, and magnetic beads (Protein G Dynabeads) immobilized with 2 µg of the monoclonal antibody recognizing CD9 prepared in the inventors' company were added thereto. After reacting at 4° C. overnight, the magnetic beads were washed three times with PBS, and the samples were eluted with the sample buffer (containing SDS) from the magnetic beads to use as samples for western blotting. These samples were analyzed by western blotting using the biotinylated anti-CD9 antibody.

Figure 2B:
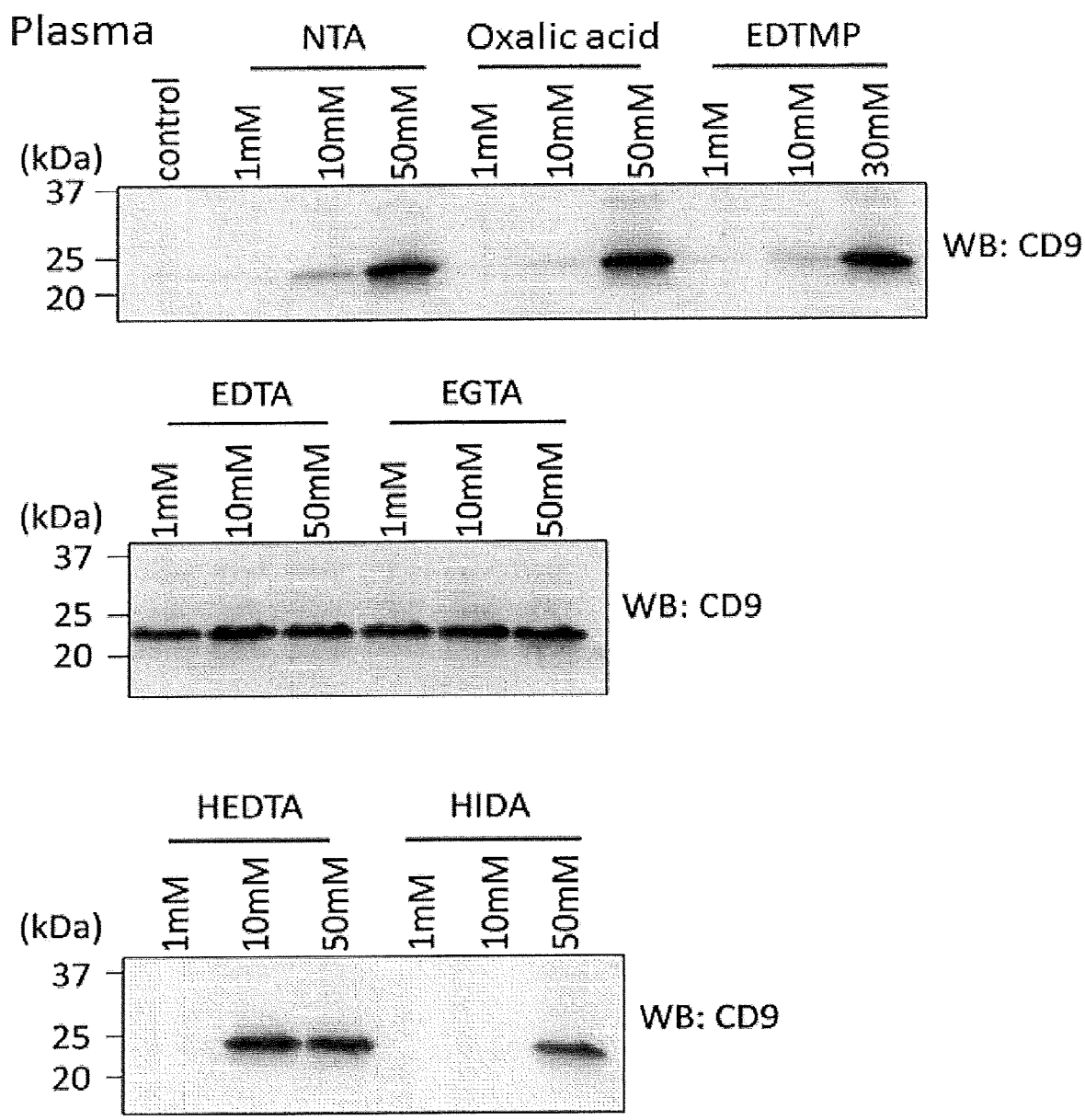
FIG. 2B shows a western blotting with the biotinylated anti-CD9 antibody of samples obtained from the immunoprecipitation method of plasma specimens diluted with each chelating agent at each concentration in Example 2.

As a result, all of the chelating agents used showed recovery of exosomes by immunoprecipitation both in the serum specimens (FIG. 2A) and the plasma specimens (FIG. 2B). In addition, as the concentration of the chelating agent increased, the amount of the immunoprecipitated exosomes increased. In particular, the immunoprecipitation amounts of exosomes drastically increased under the conditions of adding 30 mM EDTMP, 50 mM EDTA, EGTA, HEDTA, NTA and oxalic acid (FIGS. 2A and 2B).

These results demonstrated that all of the chelating agents used demonstrate the recovery of exosomes by immunoprecipitation, and that the chelating agent has an effect of enhancing the efficiency of exosome recovery by the immunoprecipitation as the concentration of the chelating agent increases.

Example 3

The effects of chelating agent on efficiency of exosome recovery in preparation of exosomes by an ultracentrifugation method were investigated.

300 µL of a plasma specimen (two specimens #1 and #2) was diluted with 600 µL of PBS or EDTA and EGTA-containing PBS (final concentration of EDTA and EGTA: each 50 mM), followed by being left to stand at room temperature for 30 minutes, and then centrifuged at 20,000×g at 4° C. for 15 minutes. Subsequently, the resulting supernatant was centrifuged at 100,000×g at 4° C. for 3 hours. The supernatant was discarded, and PBS was newly added to resuspend the precipitate. Then, the resuspension was centrifuged at 150,000×g at 4° C. for one hour. The supernatant was discarded, and PBS was newly added to resuspend the precipitate, which was then used as a sample. Proteins in the sample were quantitatively measured by BCA Assay Kit (manufactured by Thermo Scientific). The sample was diluted with the sample buffer (containing SDS) to use as the sample for western blotting. 1.5 µg as a protein amount of each sample was used for the western blotting. CD9 in the sample was detected by the biotinylated anti-CD9 antibody.

Figure 3:
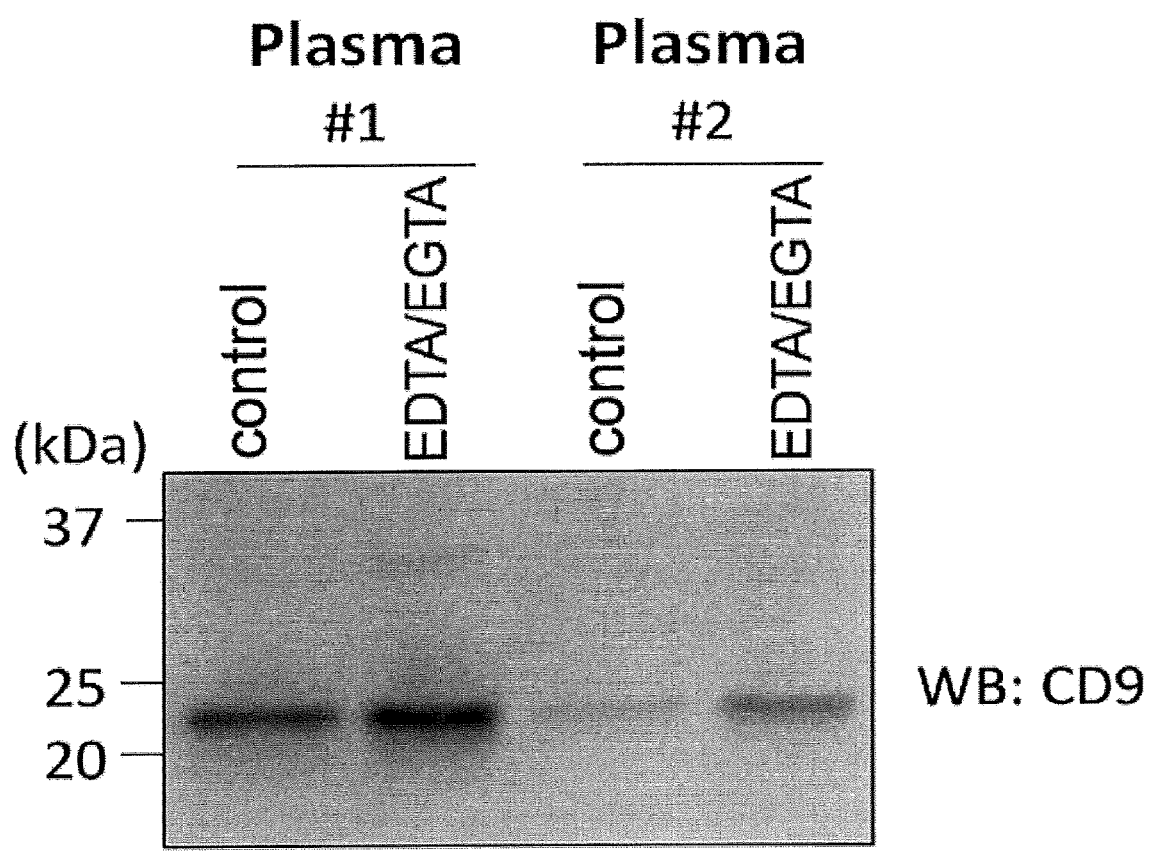
FIG. 3 shows a western blotting with the biotinylated anti-CD9 antibody of samples obtained from an ultracentrifugation method of serum specimens diluted with PBS ("control") or EDTA/EGTA/PBS ("EDTA/EGTA") in Example 3.

As a result, the amount of CD9 in an equal protein amount increased depending on the recovery condition using the chelating agent (Table 1 and FIG. 3).

This result demonstrated that a purity of the exosomes in a recovered product increased and the efficiency of exosome recovery increased by treatment with the chelating agent also in the ultracentrifugation method. This is thought to be because the concomitant substances present on the surface of the exosome were decreased by the treatment with the chelating agent.

TABLE 1

|  |  | Concentration |
|---|---|---|
| Plasma #1 | Control | 453 µg/mL |
|  | EDTA/EGTA | 195 µg/mL |
| Plasma #2 | Control | 2347 µg/mL |
|  | EDTA/EGTA | 827 µg/mL |

Example 4

In the recovery of exosomes derived from cultured cells by the ultracentrifugation method, the effects by the treatment with chelating agent on the efficiency of exosome recovery was investigated.

A culture supernatant of human colon adenocarcinoma cell line LoVo cultured in serum-free medium for three days was centrifuged at 2,000×g at 4° C. for 5 minutes, then filtrated through a 0.22 µm filter (manufactured by Millipore), and further concentrated using Amicon Ultra-15 (manufactured by Millipore). The concentrated sample was centrifuged at 20,000×g at 4° C. for 15 minutes. Subsequently, the resulting supernatant was centrifuged at 100,000×g at 4° C. for one hour. The supernatant was discarded, and PBS or 50 mM EDTA/50 mM EGTA/PBS was added to resuspend the precipitate. The resuspension was centrifuged at 150,000×g at 4° C. for one hour. The supernatant was discarded, and PBS or 50 mM EDTA/50 mM EGTA/PBS was added to resuspend the precipitate, which was then used as a sample. The number and distribution of particles in the sample were measured by NanoSight (manufactured by Malvern Instruments). The detections of CD9 and CEA, which is reported to be present in exosomes (Dai et al., Clin. Cancer Res., 2005, Oct. 15; 11(20): 7554-63), in the sample were carried out by western blotting using the biotinylated anti-CD9 antibody and an anti-CEA antibody (manufactured by Abcam).

Figure 4A:
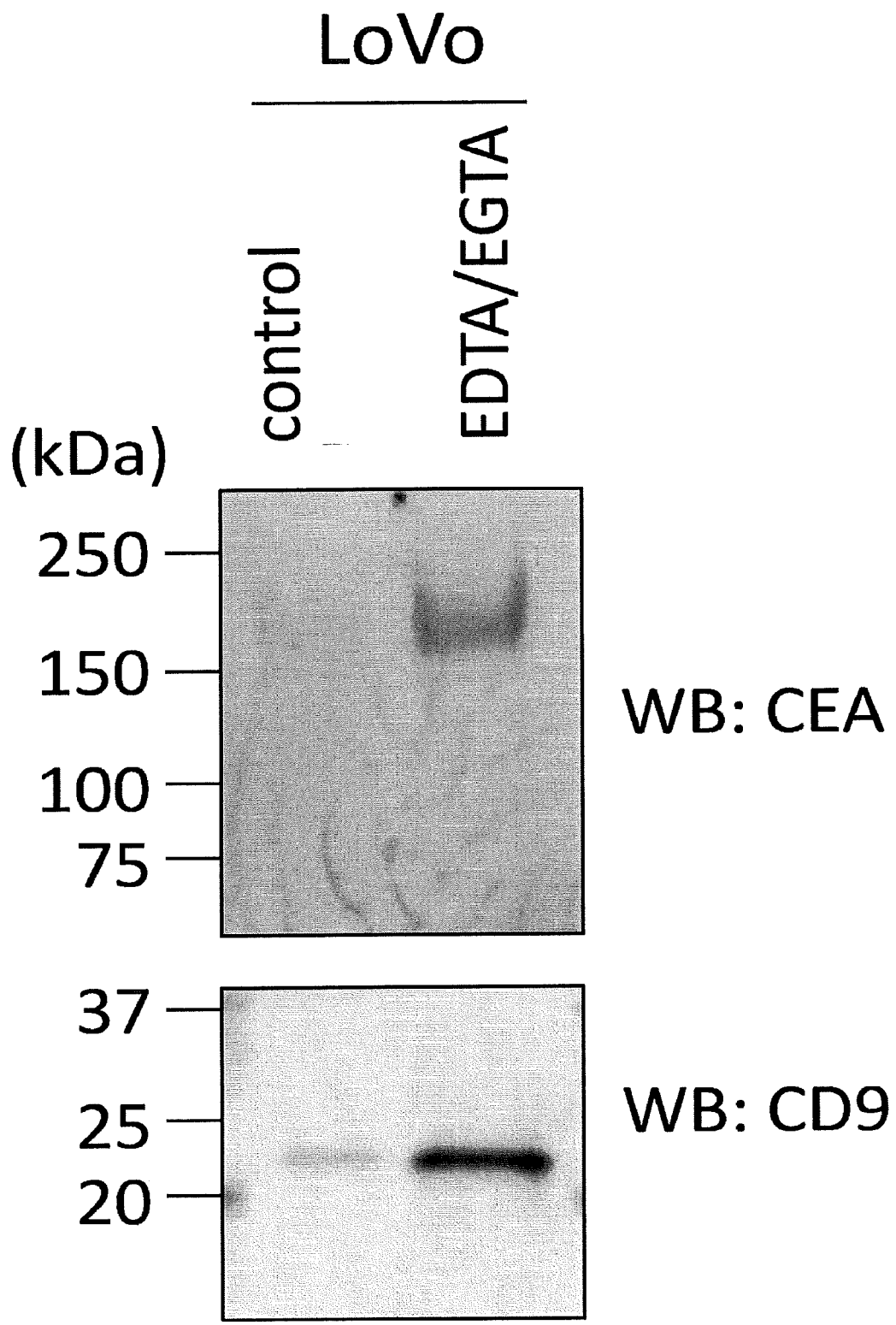
FIG. 4A shows a western blotting with an anti-CD9 antibody or an anti-CEA antibody of samples obtained by ultracentrifuging a culture supernatant of a human colon adenocarcinoma cell line LoVo, resuspending an obtained precipitate, ultracentrifuging the resuspension again, and resuspending an obtained precipitate in Example 4. The precipitates were resuspended in PBS ("control") or EDTA/EGTA/PBS ("EDTA/EGTA").
Figure 4B:
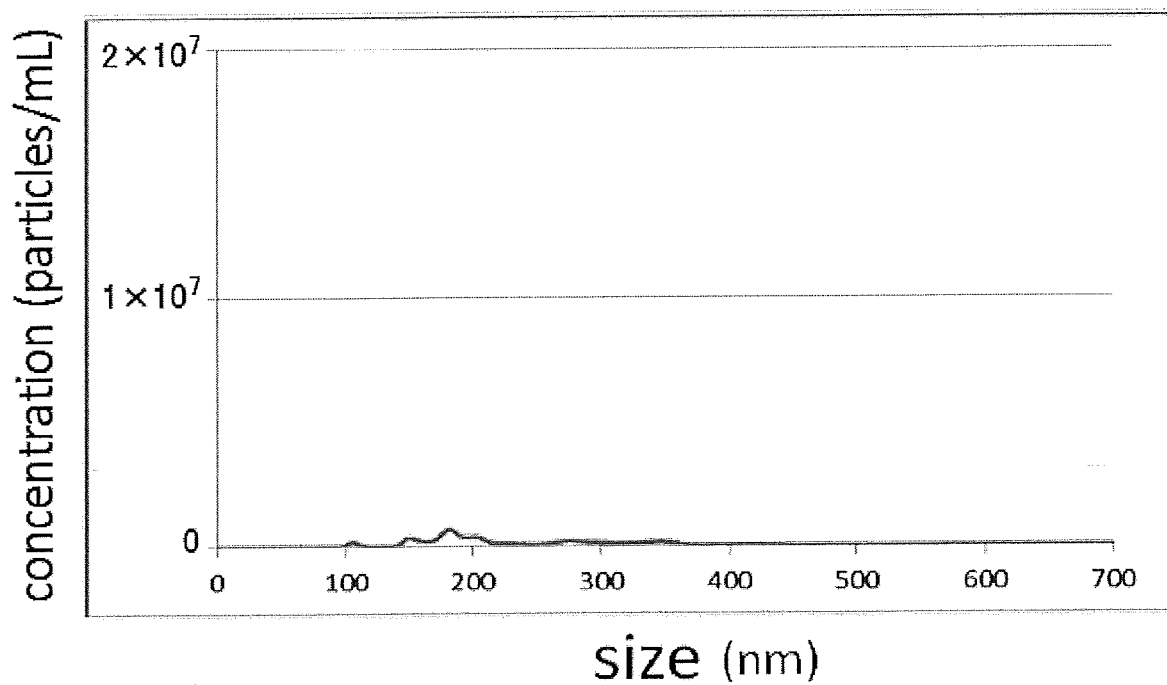
FIG. 4B shows particle counts and a particle diameter distribution measured in the samples obtained by ultracentrifuging the culture supernatant of the human colon adenocarcinoma cell line LoVo, resuspending an obtained precipitate, ultracentrifuging the resuspension again, and resuspending an obtained precipitate in Example 4. The precipitates were resuspended in PBS ("control") or EDTA/EGTA/PBS ("EDTA/EGTA").
Figure 4B:
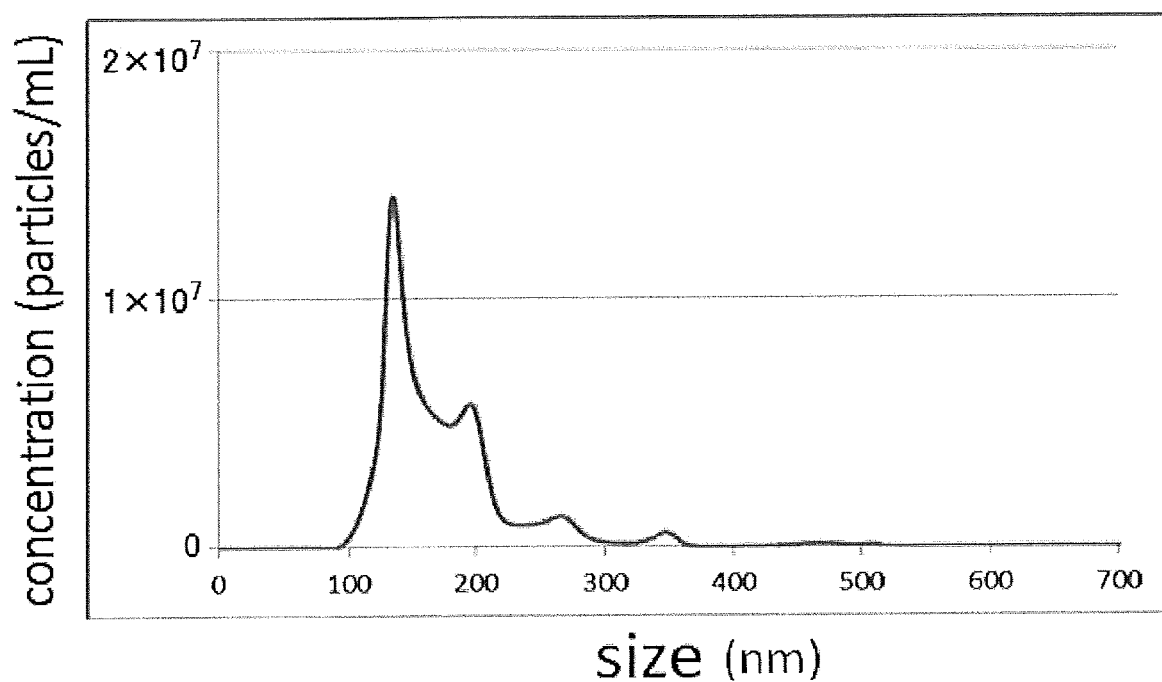

As a result, the protein amounts of the exosome markers (CD9 and CEA) increased under the recovery condition using chelating agent in view of the result of the western blotting (FIG. 4A). In view of the result of NanoSight, the particles having a size of 100 to 200 nm (thought to indicate the exosomes) remarkably increased under the recovery condition using the chelating agents (Table 2, FIG. 4B).

These results demonstrated that the treatment with the chelating agents upon being resuspended dramatically improved the amount of the recovered exosomes in the exosome recovery by the ultracentrifugation method. This is thought to be because the concomitant substances were decreased by the treatment with the chelating agents to facilitate the resuspension of exosomes thereby increasing the efficiency of exosome recovery.

TABLE 2

| Particles/mL | Control | EDTA/EGTA | versus Control |
|---|---|---|---|
| LoVo | $5.04 \times 10^7$ | $7.40 \times 10^8$ | 1468% |

Example 5

The effects of the treatment with chelating agent and the influences of concomitant substance contamination were investigated in exosome recovery by an immunoprecipitation method.

A culture supernatant of human pancreatic adenocarcinoma cell line BxPC-3 cultured in serum-free medium for three days and a sample obtained by adding 20 mg/mL of albumin (manufactured by Millipore) to the culture supernatant were prepared. 500 µL of these samples were diluted with PBS or EDTA and EGTA-containing PBS (final concentration of EDTA and EGTA: each 50 mM) in an equal amount, then left to stand at room temperature for 30 minutes, and further centrifuged at 20,000×g at 4° C. for 15 minutes. The supernatant was transferred to a new tube, and magnetic beads (Protein G Dynabeads) to which 2 µg of the monoclonal antibody recognizing CD9 prepared in the inventors' company had been immobilized were added thereto.

After the rotation reaction at 4° C. overnight, the magnetic beads were washed three times with PBS, and 40 µL of BRUB (Britton & Robinson Universal Buffer) was added to elute particles from the magnetic beads. After leaving to stand at room temperature for 10 minutes, the magnetic beads were magnetically collected. The recovered supernatant was diluted with PBS, and the number and size distribution of the particles were measured by NanoSight (manufactured by Malvern Instruments).

Figure 5:
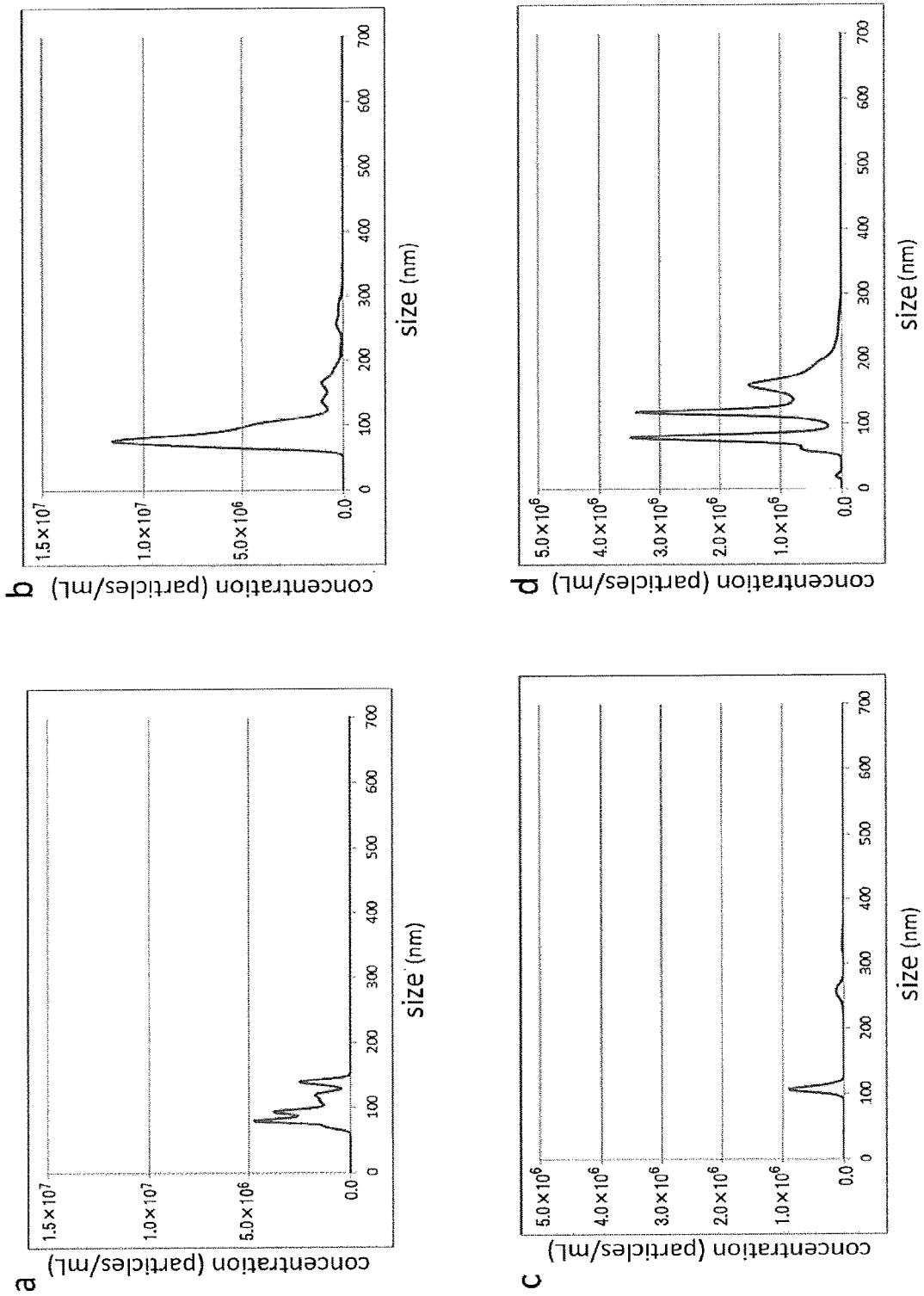
FIG. 5 shows particle counts and particle diameter distributions in exosome recovery samples obtained from a culture supernatant of a human pancreatic adenocarcinoma cell line BxPC-3 by the immunoprecipitation method in Example 5. Culture supernatants to which a concomitant substance (albumin) was not added (a and b), and was added (c and d), and culture supernatants to which EDTA/EGTA was added (b and d) and was not added (a and c) are shown.

As a result, in the absence of albumin, the number of particles recovered under the condition of adding the chelating agents increased compared with the condition of adding no chelating agent (Table 3, FIGS. 5a and 5b). Even in the presence of albumin, the number of particles recovered under the condition of adding the chelating agents also increased compared with the condition of adding no chelating agent (Table 3, FIGS. 5c and 5d). Under the condition of the absence of the chelating agent, the number of particles recovered in the presence of albumin decreased to about 10% compared with that in the absence of albumin (Table 3, FIGS. 5a and 5c). However, under the condition of adding the chelating agent, the decrease of the number of particles in the presence of albumin was about 40% compared with that in the absence of albumin (Table 3, FIGS. 5b and 5d).

These results have demonstrated that the chelating agent has the effect of enhancing the efficiency of exosome recovery either in the presence or absence of albumin as the concomitant substance. This suggests that albumin present around the exosomes prevents the recovery of the exosomes, but the chelating agent has the effect of inhibiting such a prevention, and accordingly the efficiency of exosome recovery is enhanced.

TABLE 3

| Particles/mL | Control | EDTA/EGTA | versus Control |
|---|---|---|---|
| No addition of albumin | $1.61 \times 10^8$ | $4.32 \times 10^8$ | 268% |
| Addition of albumin | $1.56 \times 10^7$ | $1.69 \times 10^8$ | 1083% |

Example 6

It was confirmed by a proteomics analysis that adsorption of concomitant substances to exosomes was inhibited by the treatment of an exosome-containing sample with a chelating agent.

300 µL of a serum specimen was diluted with 600 µL of PBS or EDTA and EGTA-containing PBS (final concentration of EDTA and EGTA: each 50 mM), left to stand at room temperature for 30 minutes, and then centrifuged at 20,000×g at 4° C. for 15 minutes. The supernatant was transferred to a new tube, and magnetic beads (Protein G Dynabeads) to which 2 µg of the antibody recognizing CD9 prepared in the inventors' company had been immobilized or magnetic beads (Protein G Dynabeads) to which no antibody was immobilized were added thereto. After the rotation reaction at 4° C. overnight, the magnetic beads were washed three times with PBS, an eluent solution was eluted from the magnetic beads, and the sample buffer (containing SDS) was added thereto, followed by performing SDS-PAGE.

After cutting out 11 bands/lane from a gel after the electrophoresis, the cut out gel was washed with water and dehydrated with acetonitrile (manufactured by Thermo Fisher Scientific). The gel was completely dried by a centrifugal evaporator (manufactured by Tokyo RIKAKIKAI Co., Ltd.), and then reduced with 50 µL of 0.01 M DTT/100 mM ammonium bicarbonate (manufactured by Sigma Aldrich) at 56° C. for 45 minutes. The gel was back to room temperature, 2 µL of 0.25 M iodoacetamide (manufactured by Wako Pure Chemical Industries Ltd.)/100 mM ammonium bicarbonate was added thereto, and the mixture was reacted at room temperature in a dark place for 15 minutes. The supernatant was removed, and then the gel was washed with 50 µL of 100 mM ammonium bicarbonate, and further washed with 50 µL of 50 mM ammonium bicarbonate/50% acetonitrile, followed by being washed with 30 µL of 100% acetonitrile and dried by centrifugal evaporator.

To the resulting gel, 20 μL of 0.1% Rapigest SF reagent (manufactured by Waters)/50 mM ammonium bicarbonate was added, and the mixture was reacted at 37° C. for 10 minutes. Subsequently, the supernatant was removed, and the gel was dried by the centrifugal evaporator. To the dried gel, 20 μL of 20 ng/μL of Trypsin/Lys-C Mix, Mass Spec Grade (manufactured by Promega) diluted with 50 mM ammonium bicarbonate was added, and penetrated into the gel on ice for 15 minutes. After adding 20 μL of 50 mM ammonium bicarbonate so that the gel was not dried, the gel was incubated at 37° C. for 18 hours. To the gel after the reaction, 50 μL of 50% acetonitrile/1% TFA (manufactured by Thermo Scientific) was added, and the gel was incubated at 37° C. for 10 minutes, and subsequently an extraction liquid was collected. This process was repeated twice. Finally, 50 μL of 80% acetonitrile was added, then the gel was incubated at 37° C. for 2 minutes, and subsequently an extraction liquid was collected. All of the extraction liquids were combined into one, which was then concentrated and dried by the centrifugal evaporator to yield a peptide-containing sample.

10 μL of 0.1% formate water (manufactured by Thermo Scientific) was added to the obtained sample containing the peptides, and dissolved it. Subsequently, the sample was subjected to mass spectrometry using LC-MS (LC: manufactured by Eksigent, mass spectrometer: Triple TOF 5600+, manufactured by AB Sciex). Proteins were identified using ProteinPilotVer4.5beta (manufactured by AB Sciex).

As a result of the mass spectrometry, proteins obtained by excluding proteins identified under the condition of EDTA/EGTA dilution and CD9 antibody-binding beads and proteins identified under the condition of PBS dilution and antibody-non-binding beads from proteins identified under the condition of PBS dilution and CD9 antibody-binding beads are shown in Table 4. Various proteins shown in Table 4 were demonstrated to be those, the adsorption of which to the exosome had been inhibited by the treatment with the chelating agent.

This result demonstrated that the treatment with the chelating agent can inhibit the adsorption of various proteins to the exosomes and thus proteomics of the exosome with higher accuracy becomes possible. It is also anticipated that it becomes possible to provide the exosomes that are more homogeneous in quality by virtue of the inhibition of such adsorption.

TABLE 4

Proteins which were inhibited for adsorption to exosomes by the chelating agent treatment

| | Accession | Name |
|---|---|---|
| 1 | Q96C24 | Synaptotagmin-like protein 4 OS = Homo sapiens GN = SYTL4 PE = 1 SV = 1 |
| 2 | P04004 | Vitronectin OS = Homo sapiens GN = VTN PE = 1 SV = 1 |
| 3 | P06493 | Cell division control protein 2 homolog OS = Homo sapiens GN = CDC2 PE = 1 SV = 2 |
| 4 | P07478 | Trypsin-2 OS = Homo sapiens GN = PRSS2 PE = 1 SV = 1 |
| 5 | P04220 | Ig mu heavy chain disease protein OS = Homo sapiens PE = 1 SV = 1 |
| 6 | P04217 | Alpha-1B-glycoprotein OS = Homo sapiens GN = A1BG PE = 1 SV = 3 |
| 7 | P01623 | Ig kappa chain V-III region WOL OS = Homo sapiens PE = 1 SV = 1 |
| 8 | P02790 | Hemopexin OS = Homo sapiens GN = HPX PE = 1 SV = 2 |
| 9 | P01008 | Antithrombin-III OS = Homo sapiens GN = SERPINC1 PE = 1 SV = 1 |

TABLE 4-continued

Proteins which were inhibited for adsorption to exosomes by the chelating agent treatment

| | Accession | Name |
|---|---|---|
| 10 | P00734 | Prothrombin OS = Homo sapiens GN = F2 PE = 1 SV = 2 |
| 11 | P06396 | Gelsolin OS = Homo sapiens GN = GSN PE = 1 SV = 1 |
| 12 | P09871 | Complement C1s subcomponent OS = Homo sapiens GN = C1S PE = 1 SV = 1 |
| 13 | P00751 | Complement factor B OS = Homo sapiens GN = CFB PE = 1 SV = 2 |
| 14 | P02748 | Complement component C9 OS = Homo sapiens GN = C9 PE = 1 SV = 2 |
| 15 | Q15485 | Ficolin-2 OS = Homo sapiens GN = FCN2 PE = 1 SV = 2 |
| 16 | P27169 | Serum paraoxonase/arylesterase 1 OS = Homo sapiens GN = PON1 PE = 1 SV = 2 |
| 17 | P04432 | Ig kappa chain V-I region Daudi OS = Homo sapiens PE = 4 SV = 1 |
| 18 | P01779 | Ig heavy chain V-III region TUR OS = Homo sapiens PE = 1 SV = 1 |

Example 7

The effects of the treatment with chelating agent were investigated in the recovery of urine exosomes by the immunoprecipitation method.

300 μL of a urine sample was diluted with 600 μL of PBS or EDTA and EGTA-containing PBS (final concentration of EDTA and EGTA: each 50 mM), the mixture was left to stand at room temperature for 30 minutes, and then centrifuged at 20,000×g at 4° C. for 15 minutes. The supernatant was transferred to a new tube, and magnetic beads (Protein G Dynabeads, (manufactured by Life Technologies)) to which 2 μg of the antibody recognizing CD9 prepared in the inventors' company, a surface marker of the exosome, had been immobilized were added thereto. The mixture was rotation reacted at 4° C. overnight, then the magnetic beads were washed three times with PBS-T to elute the sample from the magnetic beads, and the sample was diluted with SDS-containing sample buffer (manufactured by BIO-RAD) to use as a sample for western blotting.

The sample diluted with PBS was used as a control, the sample diluted with EDTA/EGTA/PBS was used as EDTA/EGTA, and both the samples were analyzed by the western blotting using the biotinylated anti-CD9 antibody.

Figure 6:
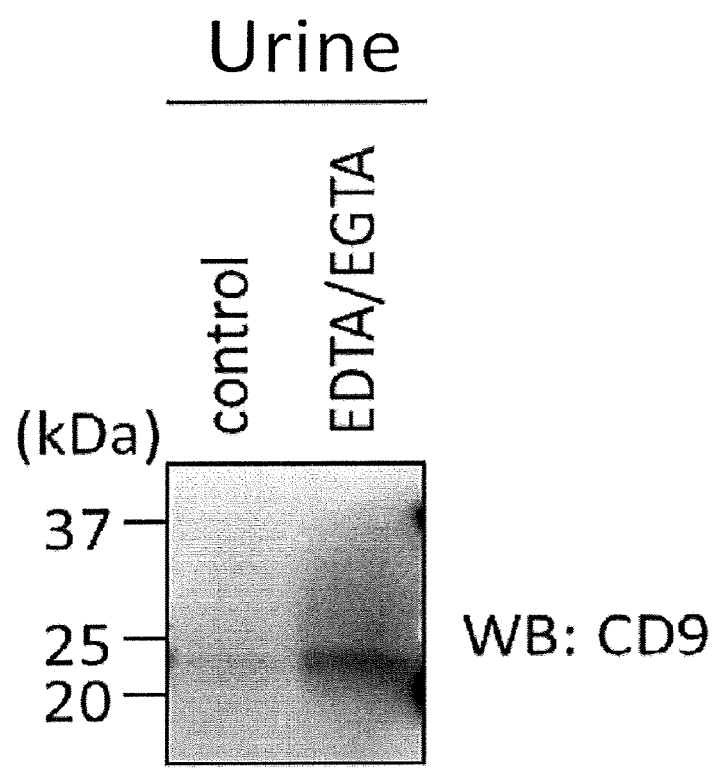
FIG. 6 shows a western blotting (WB) with the biotinylated anti-CD9 antibody of samples obtained from the immunoprecipitation method of a urine specimen diluted with PBS ("control") or EDTA/EGTA/PBS ("EDTA/EGTA") in Example 7.

As a result, an amount of immunoprecipitated exosomes (CD9) increased under the condition of adding the chelating agents (EDTA and EGTA) (FIG. 6).

This result demonstrated that the chelating agent also has the effect of enhancing the efficiency of exosome recovery in the urine sample by the immunoprecipitation method, and that the present invention is also available for the urine specimens.

Example 8

The effects of the treatment with chelating agent on recovery efficiency of exosomes derived from cow milk were investigated in the recovery by the ultracentrifugation method.

Figure 7:
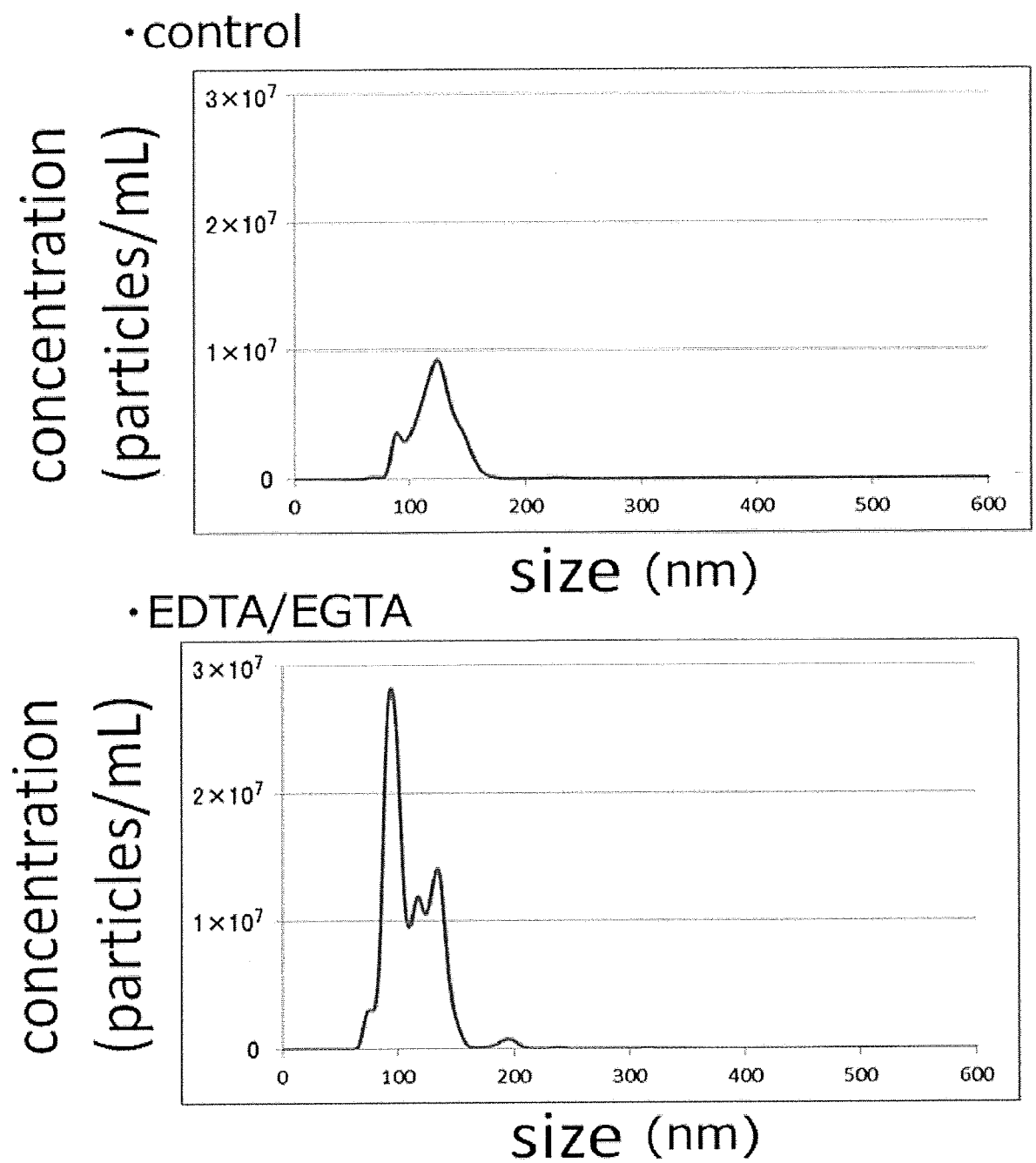
FIG. 7 shows particle counts and a particle diameter distribution measured in samples obtained by ultracentrifuging a supernatant of cow milk treated with an acetic acid, resuspending an obtained precipitate, ultracentrifuging the resuspension again, and resuspending an obtained precipitate in Example 8. The precipitates were resuspended in PBS ("control") or EDTA/EGTA/PBS ("EDTA/EGTA").

To 20 mL of commercially available cow milk, an acetic acid in an amount of 1/10 volume was added, and the mixture was mixed upside down and then centrifuged at 2,000×g at 4° C. for 5 minutes. The supernatant was filtrated sequentially through a 0.45 μm filter (manufactured by Millipore) and a 0.22 μm filter (manufactured by Millipore), followed by being concentrated using Amicon Ultra-15 (manufactured by Millipore). The concentrated sample was centrifuged at 20,000×g at 4° C. for 15 minutes. Subsequently, the supernatant was centrifuged at 100,000×g at 4° C. for one hour. The supernatant was discarded, and PBS or 50 mM EDTA/50 mM EGTA/PBS was added to resuspend the precipitate. Subsequently, the resuspension was centrifuged at 150,000×g at 4° C. for one hour. The supernatant was discarded, and PBS or 50 mM EDTA/50 mM EGTA/PBS was added again to resuspend a precipitate, which was then used as a sample. Sucrose/PBS at each concentration of 2.0 M, 1.5 M, 1.0 M and 0 M was prepared, and 1.4 mL, 1.0 mL, 1.4 mL and 0.8 mL thereof in the order of 2.0 M, 1.5 M, 1.0 M and 0 M was each added into a tube for ultracentrifugation. 200 µL of the resuspended sample was applied as a top later on sucrose/PBS, and the tubes were ultracentrifuged at 150,000×g at 4° C. for 16 hours. After the centrifugation, the particle counts and the distribution of particle sizes were measured in the recovered sample by NanoSight (manufactured by Malvern Instruments). From results of NanoSight, the number of particles having the size of 100 to 200 nm (thought to indicate the exosomes) remarkably increased under the recovery condition using the chelating agent (Table 5, FIG. 7).

This result demonstrated that the treatment with the chelating agent upon resuspension dramatically improved the amount of the recovered exosomes in the recovery of the exosomes from the cow milk by the ultracentrifugation method. This is thought to be because the concomitant substances were decreased by the treatment with the chelating agent to facilitate the resuspension of exosomes, thereby increasing the efficiency of exosome recovery.

TABLE 5

| Particles/mL | Control | EDTA/EGTA | versus Control |
| --- | --- | --- | --- |
| Cow milk | $3.94 \times 10^8$ | $9.98 \times 10^8$ | 253% |

The invention claimed is:

1. A method of recovering extracellular vesicles, the method comprising:
   (1) adding a chelating agent to a sample comprising extracellular vesicles, thereby obtaining a solution comprising at least 40 mM of the chelating agent and the extracellular vesicles, wherein the sample comprising extracellular vesicles comprises a culture supernatant or a body fluid;
   (2) treating the sample comprising extracellular vesicles with the chelating agent in the solution;
   (3) separating the solution obtained in (2) into (i) a liquid portion comprising the chelating agent and (ii) a precipitation portion comprising the extracellular vesicles;
   (4) removing the liquid portion comprising the chelating agent; and
   (5) recovering the precipitation portion comprising the extracellular vesicles,
   wherein the chelating agent is at least one selected from the group consisting of ethylenediaminetetraacetic acid (EDTA), glycoletherdiaminetetraacetic acid (EGTA), hydroxyethyl ethylenediaminetriacetic acid (HEDTA), hydroxyethyliminodiacetic acid (HIDA), oxalic acid, ethylenediaminetetra (methylenephosphonic acid) (EDTMP), a salt thereof, and a mixture thereof.

2. The method of claim 1, wherein the sample comprising extracellular vesicles is treated with 40 mM to 200 mM of the chelating agent.

3. The method of claim 1, wherein the extracellular vesicles are exosomes.

4. The method of claim 1, wherein the separating is performed by a precipitation method using an extracellular vesicle membrane-binding substance or an ultracentrifugation method of the sample comprising extracellular vesicles.

5. The method of claim 4, wherein the extracellular vesicle membrane-binding substance is an antibody against CD9.

6. The method of claim 4, wherein the extracellular vesicle membrane-binding substance is bound to a solid phase.

7. The method of claim 4, wherein the extracellular vesicle membrane-binding substance is bound to magnetic beads.

8. The method of claim 1, wherein the sample comprising extracellular vesicles is the body fluid or the culture supernatant.

9. The method of claim 1, wherein the sample comprising extracellular vesicles is a blood sample, urine, or a breast fluid.

10. A method of analyzing extracellular vesicles, the method comprising:
    (1) recovering extracellular vesicles by the method of claim 1, wherein the extracellular vesicles comprise a component to be analyzed; and
    (2) analyzing the recovered extracellular vesicles,
    (i) wherein when the recovered extracellular vesicles comprise the component to be analyzed, the component in the recovered extracellular vesicles is analyzed by at least one method selected from the group consisting of an immunoassay, hybridization method, gene amplification method, mass spectrometry, proteome analysis and metabolome analysis, or
    (ii) the recovered extracellular vesicles are analyzed with at least one instrument selected from the group consisting of a particle analytical instrument, an electron microscope and a flow cytometer.

11. The method of claim 10, wherein the recovered extracellular vesicles comprise a protein, and the protein in the recovered extracellular vesicles is analyzed by at least one method selected from the group consisting of an immunoassay, mass spectrometry and proteome analysis.

12. The method of claim 1, wherein the sample is treated with the chelating agent for at least one minute.

13. The method of claim 1, wherein the treating is performed at from 15 to 30° C.

14. The method of claim 1, wherein the sample comprising extracellular vesicles is treated with at least 40 mM of EDTA.

15. The method of claim 1, wherein the sample comprising extracellular vesicles is treated with at least 40 mM of EGTA.

16. The method of claim 1, further comprising preparing the sample comprising extracellular vesicles before (1), wherein the sample comprising extracellular vesicles is plasma.

17. The method of claim 1, wherein the sample comprising extracellular vesicles comprises a sample other than urine.

18. The method of claim 1, further comprising suspending the recovered precipitation portion in a solution which does not comprise a chelating agent, thereby obtaining a suspension which comprises the extracellular vesicles and which does not comprise a chelating agent.

19. A method of recovering extracellular vesicles, the method comprising:

(1) adding a chelating agent to a sample comprising extracellular vesicles, thereby obtaining a solution comprising at least 40 mM of the chelating agent and the extracellular vesicles, wherein the sample comprising extracellular vesicles comprises a culture supernatant or a body fluid;

(2) treating the sample comprising extracellular vesicles with the chelating agent in the solution;

(3) separating the solution obtained in (2) into (i) a liquid portion comprising the chelating agent and (ii) a precipitation portion comprising the extracellular vesicles by a precipitation method using an extracellular vesicle membrane-binding substance;

(4) removing the liquid portion comprising the chelating agent; and (5) recovering the precipitation portion comprising the extracellular vesicles, wherein the chelating agent is at least one selected from the group consisting of ethylenediaminetetraacetic acid (EDTA), glycoletherdiaminetetraacetic acid (EGTA), hydroxyethyl ethylenediaminetriacetic acid (HEDTA), hydroxyethyliminodiacetic acid (HIDA), oxalic acid, ethylenediaminetetra (methylenephosphonic acid) (EDTMP), a salt thereof, and a mixture thereof.

20. The method of claim 19, wherein the extracellular vesicle membrane-binding substance is bound to magnetic beads.

21. The method of claim 20, wherein the precipitation portion comprises magnetic beads bound with the extracellular vesicles via the extracellular vesicle membrane-binding substance, and further comprising eluting the extracellular vesicles from the recovered precipitation portion.

22. A method of recovering extracellular vesicles, the method comprising:

(1) adding a chelating agent to a sample comprising extracellular vesicles, thereby obtaining a solution comprising at least 40 mM of the chelating agent and the extracellular vesicles, wherein the sample comprising extracellular vesicles comprises a culture supernatant or a body fluid;

(2) treating the sample comprising extracellular vesicles with the chelating agent in the solution;

(3) separating the solution obtained in (2) into (i) a liquid portion comprising the chelating agent and (ii) a precipitation portion comprising the extracellular vesicles by ultracentrifugation;

(4) removing the liquid portion comprising the chelating agent; and (5) recovering the precipitation portion comprising the extracellular vesicles, wherein the chelating agent is at least one selected from the group consisting of ethylenediaminetetraacetic acid (EDTA), glycoletherdiaminetetraacetic acid (EGTA), hydroxyethyl ethylenediaminetriacetic acid (HEDTA), hydroxyethyliminodiacetic acid (HIDA), oxalic acid, ethylenediaminetetra (methylenephosphonic acid) (EDTMP), a salt thereof, and a mixture thereof.

* * * * *